United States Patent [19]
Chase et al.

[11] Patent Number: 5,527,270
[45] Date of Patent: Jun. 18, 1996

[54] MASTECTOMY BANDAGE

[76] Inventors: Beverly J. Chase, 14820 S.E. 111th Pl., Renton, Wash. 98059; Emeline E. Yelland, 10703 - 148th Ave S.E., Renton, Wash. 98509-4232; Barbara A. Schellert, 3506 Park Ave., Renton, Wash. 98056

[21] Appl. No.: 205,275
[22] Filed: Mar. 1, 1994
[51] Int. Cl.⁶ .................................................. A61F 13/00
[52] U.S. Cl. ................................ 602/41; 602/61; 602/63; 602/75; 602/79; 450/58; 450/63
[58] Field of Search ................................. 602/41–43, 75, 602/76, 77, 78, 61, 63; 128/D15; 2/311, 371; 450/58, 63

[56] References Cited

U.S. PATENT DOCUMENTS

| | | | |
|---|---|---|---|
| 3,054,000 | 9/1992 | Lizio | 602/75 |
| 3,968,803 | 7/1976 | Hyman . | |
| 4,665,909 | 5/1987 | Trainor | 602/76 |
| 4,957,466 | 9/1990 | Hopps | 450/85 |
| 5,098,331 | 3/1992 | Corrado | 450/58 |

FOREIGN PATENT DOCUMENTS 2095559  10/1992  United Kingdom .................... 602/75

*Primary Examiner*—Joe Cheng
*Assistant Examiner*—Kim M. Lee
*Attorney, Agent, or Firm*—Christensen, O'Connor, Johnson & Kindness

[57] ABSTRACT

A bandage for use to apply pressure to the wound area of a patient who has undergone a mastectomy includes a main body panel formed from a fabric that is non-elastic and breathable. The bandage is secured adjacent the side of the body of the patient to avoid the formation of a seam adjacent the wound area, yet allow application and removal of the bandage by the patient without assistance and with minimal pain and discomfort. An elastic member enables adjustment of the bandage for proper fit around the torso of the patient and ensures the application of adequate pressure. The bandage is configured so that the material that contacts the person's skin is non-elastic and breathable for increased comfort.

12 Claims, 2 Drawing Sheets

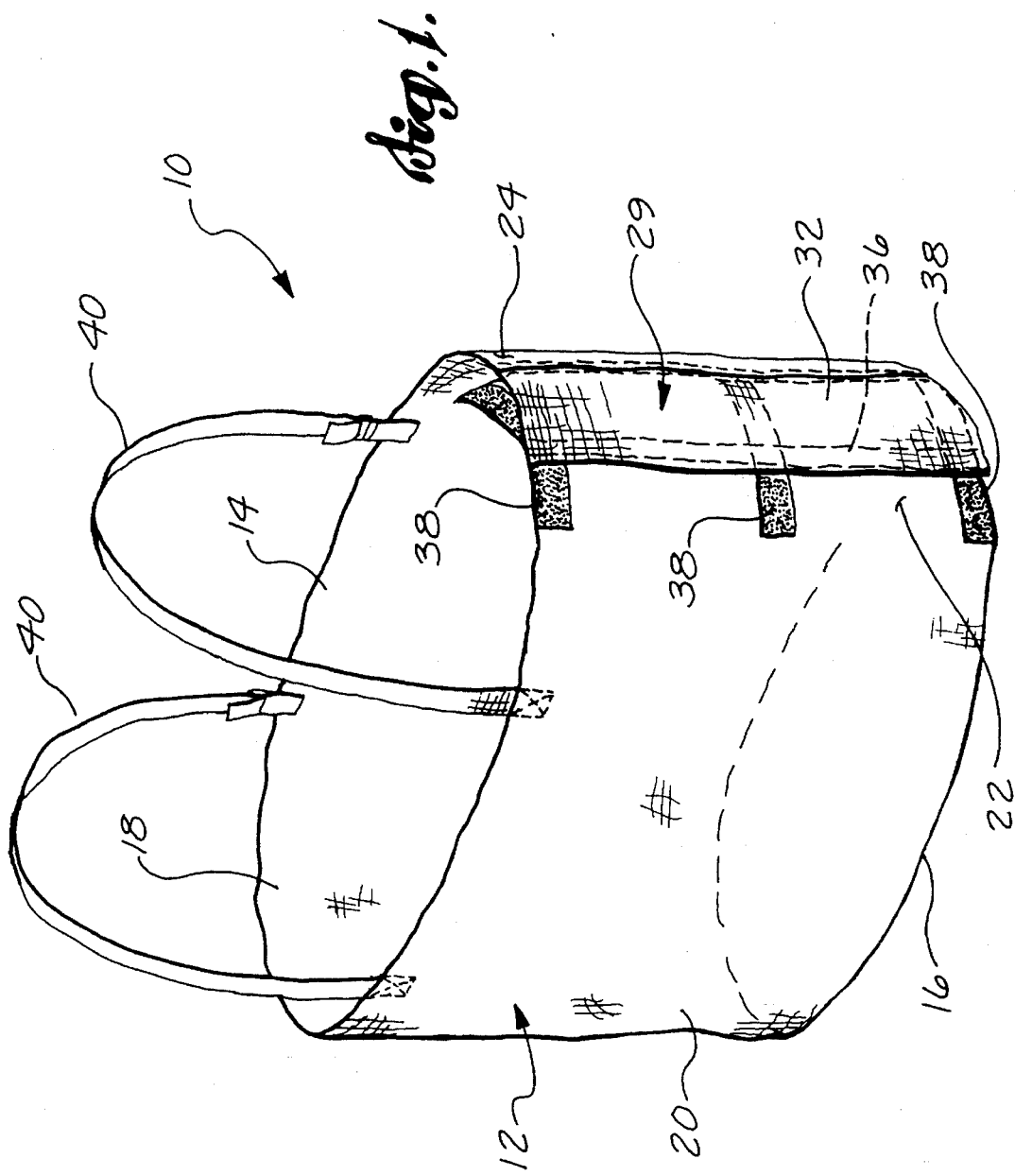

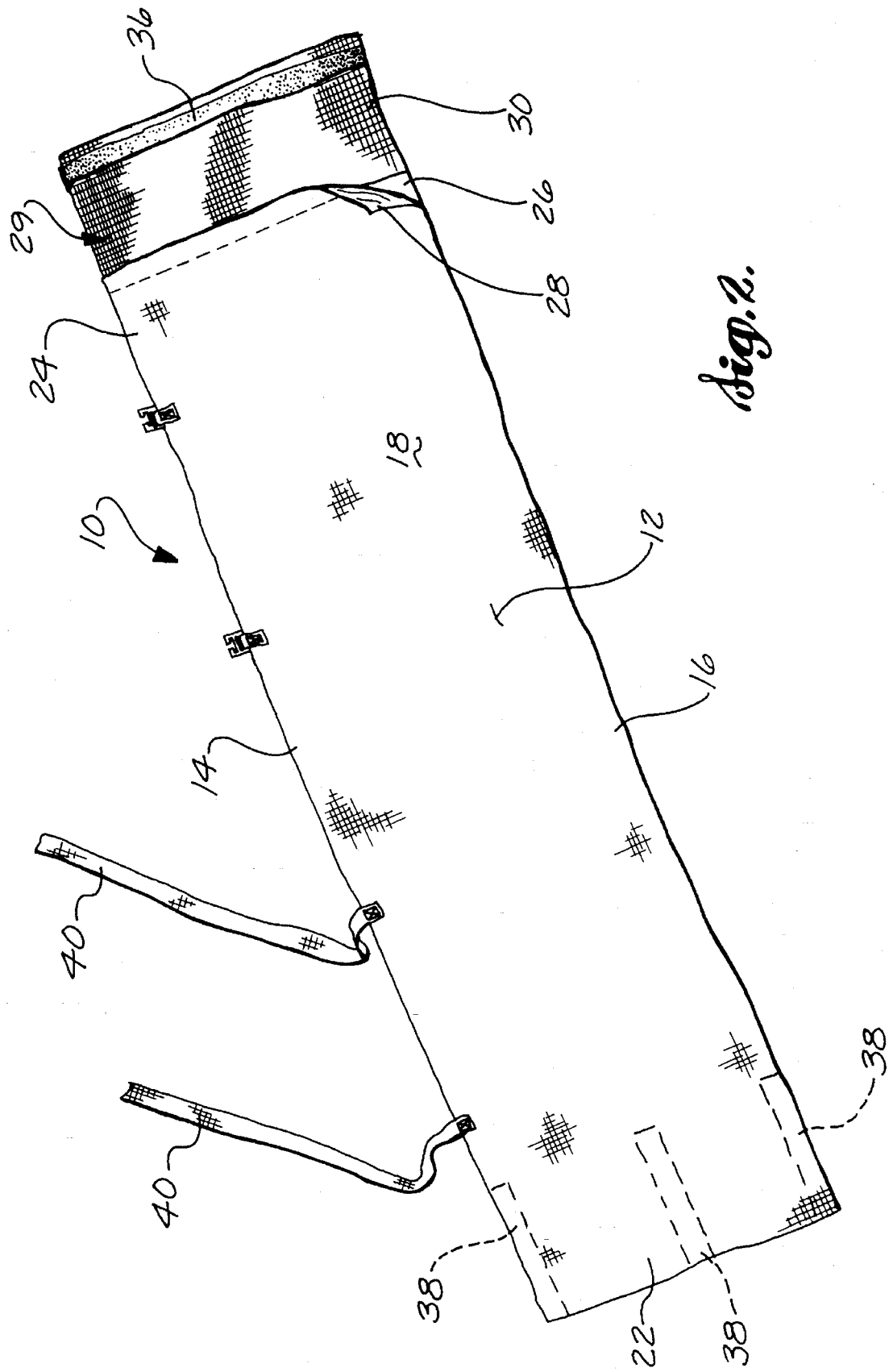

MASTECTOMY BANDAGE

FIELD OF THE INVENTION

The present invention relates to a medical bandage, and more particularly, to a bandage for use to secure a dressing over the chest area of a person. Although the bandage of the present invention is described in relation to a patient who has undergone a mastectomy, it should be understood that the present invention is not limited to such use but may be employed to apply pressure over other types of wounds and to other areas of the body.

BACKGROUND OF THE INVENTION

After a mastectomy, it is necessary for the mastectomy patient to wear a dressing over the wound area. The patient is required to wear the dressing throughout the recovery period which typically is about four to six weeks. The dressing must be changed at least once every day. Initially the patient is assisted by hospital personnel or other persons in changing the dressing. However, in view of the relatively lengthy recovery period, it is desirable that the patient eventually be able to change the dressing by herself with minimal pain and discomfort, since oftentimes there may not be anyone available to assist the patient. Moreover, since a dressing is required continually throughout the recovery period, it is especially important that the means used to secure the dressing to the patient be comfortable. For example, it should not chafe the skin nor trap excessive moisture against the skin. Furthermore, the patient experiences significant swelling in the wound area. This swelling decreases over time. The bandage should be easily adjustable to achieve proper fit in conformance with the amount of swelling experienced at any given time.

It is known to use nonadhesive bandages (i.e., bandages that do not use adhesive tape) that encircle the chest of a patient to secure a dressing to a mastectomy area. However, these bandages are characterized by the use of elastic material that contacts the skin and tends to entrap excessive moisture so as to create further discomfort for the person. Elastic material returns with force to substantially, if not completely, its original shape when released after stretching. As a result of this tendency to return to its original shape, elastic material when pulled over a surface exerts pronounced pressure on that surface. Thus, a bandage that uses elastic material to cover a wound applies a substantial amount of pressure to the area of the body contacting the elastic material. In contrast, a non-elastic material tends to resist stretching or to lose shape upon stretching (i.e., it does not have a tendency to rebound to its original shape).

Although some elastic materials breathe to a limited extent, they tend to entrap significantly more moisture against the skin as compared to a breathable material such as cotton, gauze, flannel, or other fabric materials. Also, elastic materials tend to create a "binding" sensation that many persons find uncomfortable. Moreover, in some prior art bandages, the edges of the elastic material tend to roll up and/or the elastic material chafes the skin. Furthermore, some prior art nonadhesive bandages cause undue discomfort in that they fasten at the center of the person's chest, thereby forming a seam that lies adjacent the mastectomy area. The mastectomy wound and surrounding areas are extremely tender, especially during the early part of the recovery period. The pulling of the two sides of the seam adjacent the mastectomy area may cause undue pain and discomfort.

U.S. Pat. No. 3,561,442 to Goswitz describes a mastectomy compression bandage consisting of a strip that fastens at the front. The strip includes an elastic portion that covers the area of the mastectomy. A brassiere cup made of non-elastic material is provided to cover the remaining breast. This brassiere cup would appear to limit the range of adjustablility of the bandage.

U.S. Pat. No. 5,011,452 to Kelly describes a brassiere for use during sporting activities or for use by persons in post-surgical rehabilitation. In some embodiments, the brassiere is configured in a closed loop form. In order to apply or remove the brassiere, the person must slide the brassiere over her head and neck as if it was a t-shirt. In another embodiment, the brassiere is provided with an opening at the front that is closed by hook/eye fasteners or hook and loop fasteners. All embodiments are provided with a drawstring on the front panel for tightening the front panel around the chest. It would seem the tightened drawstring causes discomfort in the mastectomy area. Further, the back panel of the brassiere is made of an elastic material.

A mastectomy bandage providing increased comfort and that is easily adjusted to apply adequate pressure in conformance with the amount of swelling experienced at any given time is desirable.

SUMMARY OF THE INVENTION

The present invention is a mastectomy bandage that provides increased comfort and is easily adjusted to accommodate changes in the amount of swelling in the wound area. Moreover, the bandage has a simple and inexpensive construction.

The bandage comprises a main body panel formed of a non-elastic, breathable material. The main body panel is configured to encircle the torso of a person, the ends of the main body panel being located adjacent one side of the person's body when the bandage is applied. An elastic member is attached at one side of the main body panel. When the bandage is applied, the main body panel is wrapped around the chest of the person and secured on the side of the person's body on which surgery was not performed (assuming the person has undergone only a single mastectomy). First and second shoulder straps attached to the main body panel further serve to hold the bandage in place. The provision of the fastening means at the side of the person's body minimizes the pain and discomfort in the mastectomy area, yet enables the person, in the case of a single mastectomy, to use the arm on the side of the body that has not been operated on to easily apply and remove the bandage. It should be apparent that the bandage of the present invention may be used by a patient who has undergone a double mastectomy. In that case, the patient most likely will require assistance applying and removing the bandage, so the bandage could be configured to be closed at some place other than the side of the body, e.g., at the back.

Use of a hook and loop fastener as a securing means is preferable because it allows a wide range of adjustability to accommodate variations in swelling and is easy to manipulate. When the bandage is applied, the inner side of the elastic member at least substantially, and preferably completely, overlaps the outer side of the main body panel so that very little, and preferably none, of the elastic member contacts the skin of the person. Since substantially all, if not all, of the material that contacts the skin of the person is non-elastic and breathable, greater comfort is achieved while still maintaining adequate pressure on the chest.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a perspective view of a mastectomy bandage in accordance with the present invention, with a corner of the main body panel turned back to show the overlapping relation of the elastic means and the main body panel; and FIG. 2 is a plan view of a mastectomy bandage in accordance with the present invention when the bandage is not in use and is laid flat with the inner side facing upwardly.

DETAILED DESCRIPTION OF THE PREFERRED EMBODIMENT

The mastectomy bandage 10 of the present invention will be described with reference to FIGS. 1 and 2 herein. The bandage 10 includes a main body panel 12 having a generally elongate rectangular shape when laid flat as shown in FIG. 2. It should be understood that the main body panel 12 may be formed in a variety of shapes so long as it is sufficient to cover the wound area and apply adequate pressure when the bandage is applied. The main body panel 12 is made of a non-elastic, breathable material. The material is breathable in that it permits indirect contact through the bandage between the atmosphere and the skin and wound area. Although any suitable non-elastic, breathable material may be used, the present inventor has found muslin to work especially well. The main body panel 12 has an upper edge 14, bottom edge 16, inner side 18, outer side 20, first end portion 22, and second end portion 24. Although the main body panel 12 may be a single layer of material, the present inventor has found it preferable to use a two-layer construction in order to provide greater support. As shown in FIG. 2, two pieces of material 26, 28, having substantially the identical size, are arranged so that one piece of material overlaps the other. The two pieces 26, 28 are fastened together, e.g., by sewing, along their perimeters. The width of the main body panel 12 (i.e., the dimension from the first end portion to the second end portion) is preferably equal to or slightly greater than the circumference of the person's torso. In that regard, the bandage can be made in a variety of sizes (e.g., small, medium, large), each size accommodating a range of different chest dimensions.

The mastectomy bandage 10 is further provided with elastic means to enable adjustment of the bandage to properly fit around the person's torso and ensure the application of adequate pressure. As shown in FIG. 2, the elastic means comprises an elastic strip 29 that is attached, for example, by sewing, to the second end portion 24 of the main body panel 12. This configuration is suitable when it is desired to close the bandage 10 on the right side of the body (e.g., when the patient has had a single mastectomy on the letf side). The elastic strip 29 is attached to the first end portion 22 of the main body panel 12 when it is desired to close the bandage 10 on the left side of the body (i.e., when the wound is on the right side of the body). Although the elastic strip 29 may be attached to one of the inner or outer sides 18, 20 of the main body panel 12, it has been found preferable to sandwich one end of the elastic strip 29 between the pieces 26, 28 of the main body panel 12 and then close that edge of the main body panel 12, e.g., by sewing. The elastic strip 29 has an inner side 30 and an outer side 32. The height of the elastic strip 29 preferably is approximately the same as that of the main body panel 12, but may be of a different height. However, the width of the elastic strip 29 is comparatively narrow, preferably in the range of two to five inches. The elastic strip preferably is made of a material capable of stretching both longitudinally and transversely along the strip, e.g., lycra or a nylon/lycra blend.

The mastectomy bandage 10 is configured so that it closes at one side of the person's body. It should be apparent that for other types of wounds and on other areas of the body, it may be desirable to configure the bandage to close at some location other than the side of the person's body. Although various conventional fasteners may be used, in the preferred embodiment, a hook and loop fastener such as that distributed under the trademark VELCRO is used to secure the bandage 10. For example, as shown in FIG. 2 (which is a plan view of the bandage laid open with the inner side facing upwardly), a strip of loop material 36, preferably about ¾" to 1" wide, is provided along the height of the inner side 30 of the elastic strip 29. However, on the outer side of the main body panel 12 at the first end portion 22 are provided one or more horizontal strips of hook material that cooperate with the loop material 36 to secure the bandage 10 closed. In the illustrated embodiment, three horizontal strips 38 of hook material, each about ¾" to 1" high by 5" wide, are provided at the top, center, and bottom portions of the first end portion 22 of the main body panel 12. This yields a wide range of adjustability so that a person can properly fit the bandage 10 to accommodate various degrees of swelling experienced by the person throughout the healing period. The multiple strips 38 at the top, center, and bottom of the main body panel 12 enable the person to separately adjust these areas of the bandage 10. This is particularly advantageous because swelling tends to be of different degrees in the wound area. For example, swelling may be greater near the top of the wound area and less near the bottom.

It should be apparent that the hook and loop material may be cut in other configurations. For example, a single large piece of hook material may be provided on the outer side 20 of the main body panel 12. As another example, a strip of loop material 36, preferably about ¾" to 1"wide, may be provided along the height of the inner side 30 of the elastic strip 29. On the outer side of the main body panel 12 at the first end portion 22 may be provided two or more spaced strips of hook material, preferably about ¾" to 1" wide, running along the height of the main body panel 12. The strips preferably are spaced about 1" to 1 ½" apart.

The mastectomy bandage 10 may further be provided with a pair of conventional adjustable shoulder straps 40 as is well known in the art. In the preferred embodiment, the straps 40 are attached adjacent the upper edges 14 of the front and back sides of the main body panel 12.

To apply the mastectomy bandage 10, a person arranges the bandage 10 so the first and second end portions 22, 24 of the bandage will be on the side of the body opposite the mastectomy area (assuming the person has undergone a single mastectomy). If the bandage is provided with shoulder straps 40, the user places the straps 40 over her shoulders. Then, with the arm on the side of the body opposite the mastectomy area, she pulls the end portion of the main body panel to which the elastic means is attached until a proper fit is obtained. At that point, she secures the fastening means at the side of her body. Since the elastic means overlaps the main body panel, all of the material contacting the skin is non-elastic and breathable. Moreover, no uncomfortable seam is formed near the mastectomy area. A mastectomy patient should be able to apply the bandage without assistance and with minimal pain or discomfort. Furthermore, once the bandage is applied, it is relatively comfortable.

While the preferred embodiment of the invention has been illustrated and described, it will be appreciated that various changes can be made therein without departing from the spirit and scope of the invention. Moreover, although the bandage of the present invention has been described in connection with use on the chest wound of a mastectomy patient, it should be understood that the bandage may be used on other types of wound and on other areas of the body.

The embodiments of the invention in which an exclusive property or privilege is claimed are defined as follows:

1. A mastectomy bandage for use to apply pressure to a chest portion of a person's torso, comprising:

a main body panel formed of a non-elastic, breathable material and having a top edge, a bottom edge, an inner side, an outer side, a second end portion and a central portion therebetween; said panel being configured to enwrap the person's torso beneath the shoulders with said central portion of said main body panel around one lateral side of the torso and said end portions disposed at the other lateral side of the torso;

a first shoulder strap having opposite ends attached, respectively, adjacent to said central portion of said main body panel toward said one lateral side of the torso for extending over the adjacent shoulder;

a second shoulder strap having opposite ends attached, respectively, adjacent to the first and second end portions of the main body panel toward said other lateral side of the torso for extending over the opposite shoulder;

a discrete elastic member attached and adjacent to one of the first and second end portions of the main body panel, the elastic member overlapping the main body panel when the bandage is applied so that substantially none of the elastic member contacts the person's skin; and at least one fastener configured to secure the main body panel and elastic member around the person's torso, the first and second end portions of the main body panel being located adjacent to said other lateral side of the upper trunk.

2. The bandage of claim 1 wherein the elastic member comprises an elastic strip attached to and adjacent one of the first and second end portions of the main body panel, the elastic strip having an inner side and an outer side, said inner side of the elastic strip overlapping the outer side of the main body panel when the bandage is secured so that substantially none of the elastic strip contacts the skin of the person.

3. The bandage of claim 2 wherein the elastic strip has top and bottom edges defining a height and first and second end portions defining a width, said width being in the range of two to five inches.

4. The bandage of claim 2 wherein the fastener comprises a hook/loop material.

5. The bandage of claim 4 wherein at least one piece of hook and loop material is located on the inner side of the elastic strip and at least two horizontal strips of hook and loop material are located on the outer side of the one of the first and second end portions opposite the elastic strip, the two horizontal strips being spaced at different points along the height of the end portion to which the strips are attached, the hook and loop material on the elastic strip configured to cooperate with the horizontal strips on the end portion to secure the bandage.

6. A mastectomy bandage for use to apply pressure to a chest portion of a person's body following surgery, comprising:

a main body panel formed of a non-elastic, breathable material and having a top longitudinal edge, a bottom longitudinal edge, an inner side, an outer side, a first free end portion, a second free end portion and a central portion therebetween, said panel being configured to enwrap the upper trunk of the person beneath the shoulders with said central portion of said main body panel looped around one lateral side of the upper trunk and the free end portions disposed at an opposite lateral side of the trunk;

a first shoulder strap having opposite ends attached, respectively, adjacent to the central portion of said main body panel, said first shoulder strap extending from a front of the upper trunk, over the adjacent shoulder of the person, to a rear of the upper trunk when the bandage is applied;

a second shoulder strap having opposite ends attached, respectively, adjacent to the first and second free end portions of said main body panel, said second shoulder strap extending from a front of the upper trunk, over the opposite shoulder of the person, to a rear of the upper trunk when the bandage is applied;

elastic means for enabling adjustment of the bandage around the chest portion, said elastic means being attached to one of the first and second free end portions of said main body panel such that substantially none of the elastic means contacts the person's skin when the bandage is applied; and at least one fastener configured to secure the first and second free end portions of the main body panel together along said other opposite lateral side of the upper trunk.

7. The bandage of claim 6 wherein the elastic means comprises an elastic strip attached adjacent one of the first and second end portions of the main body panel, the elastic strip having an inner side and an outer side, the inner side of the elastic strip overlapping the outer side of the main body panel when the bandage is secured so that substantially none of the elastic strip contacts the skin of the person.

8. The bandage of claim 6 wherein the fastener comprises a hook and loop material.

9. The bandage of claim 8 wherein at least one piece of hook and loop material is located on the inner side of the elastic strip and at least two horizontal strips of hook and loop material are located on the outer side of the one of the first and second end portions opposite the elastic strip, said at least two horizontal strips being spaced at different points along the height of end portion to which the strips are attached, said hook and loop material on the said inner side of said elastic strip configured to cooperate with said at least two horizontal strips on the end portion to secure the bandage around a person's chest portion.

10. The bandage of claim 7 wherein the elastic strip has top and bottom edges defining a height and first and second end portions defining a width, the width being in the range of two to five inches.

11. A mastectomy bandage adapted to encircle an upper trunk of a person to secure a dressing to wound of a patient, said upper trunk having a first and a second lateral side, comprising:

compression means having a first end portion, a second end portion and a central portion therebetween for applying pressure around the upper trunk, said compression means adapted to substantially enwrap the upper trunk of a person and being made of breathable, non-elastic material, said compression means arranged so that when wrapped around the upper trunk the first and second end portions are located on the first lateral side of the person and the central portion is located on the second lateral side of the person;

elastic means attached to said compression means at a location adjacent at the first lateral side of a person where said compression means is closed, said elastic means enabling adjustment of the bandage around the upper trunk and cooperating with the compression means to enwrap the upper trunk such that substantially none of the elastic means contacts the person's skin when the bandage is applied;

support means attached to said compression means, said support means extending from a front of the upper trunk of the person, over each shoulder of the person, to a rear of the upper trunk of the person when the bandage is applied; and fastening means for securing the bandage to the upper trunk such that the bandage is applied said fastening means are located on the first lateral side of the person.

12. The bandage of claim 11 wherein the fastening means comprises a hook and loop material.

* * * * *

UNITED STATES PATENT AND TRADEMARK OFFICE
CERTIFICATE OF CORRECTION

PATENT NO. : 5,527,270
DATED : June 18, 1996
INVENTOR(S) : B.J. Chase et al.

It is certified that error appears in the above-indentified patent and that said Letters Patent is hereby corrected as shown below:

On the title page:

| Item: | [76] 1, col. 1 | Inventors | "98509-4232" should read --98059-4232-- |
|---|---|---|---|
| Item: | [76] 1, col. 1 | Inventors | After "Park Ave." insert --N.-- |
| Item: | [56] 1, col. 1 | Refs. Cited (U.S. Pat. Docs.) | "3,054,000 9/1992" should read --3,054,000 1/1962-- |
| Item: | [56] 1, col. 1 | Refs. Cited (U.S. Pat. Docs.) | Please insert the following references: --1,532,250 4/1925 Lindemann 2,800,902 7//1957 Wiltrout ...... 128/167 3,561,442 2/1971 Goswitz ...... 128/157 3,902,503 9/1975 Gaylord Jr. .... 128/559 3,968,803 7/1976 Hyman ....... 128/482 5,011,452 4/1991 Kelly ........ 450/69 5,152,741 10/1992 Farnio ....... 602/79-- |

| COLUMN | LINE | |
|---|---|---|
| 5 (Claim 1, | 15 line 5) | After "an outer side," insert --a first end portion,-- |
| 5 (Claim 1, | 16 line 6) | "therebetween;" should read --therebetween,-- |

UNITED STATES PATENT AND TRADEMARK OFFICE
CERTIFICATE OF CORRECTION

PATENT NO. : 5,527,270
DATED : June 18, 1996
INVENTOR(S) : B.J. Chase et al.

It is certified that error appears in the above-indentified patent and that said Letters Patent is hereby corrected as shown below:

COLUMN     LINE

5              51           "said width" should read --the width--
(Claim 3,    line 3)

5              54           "hook/loop" should read --hook and loop--
(Claim 4,    line 2)

6              7            "said central" should read --a central--
(Claim 6,    line 10)

6              32           "said other opposite" should read --said opposite--
(Claim 6,    line 34)

6              49           Before "end" insert --said--
(Claim 9,    line 7)

Signed and Sealed this

Third Day of December, 1996

Attest:

BRUCE LEHMAN

*Attesting Officer*          *Commissioner of Patents and Trademarks*